United States Patent
Koonankeil et al.

(10) Patent No.: US 9,410,905 B2
(45) Date of Patent: Aug. 9, 2016

(54) NON-DESTRUCTIVE INSPECTION OF AN ARTICLE USING CROSS-SECTIONS THROUGH INTERNAL FEATURE

(71) Applicant: United Technologies Corporation, Hartford, CT (US)

(72) Inventors: James M. Koonankeil, Marlborough, CT (US); Gordon Miller Reed, Plantsville, CT (US); Rodney H. Warner, Austin, TX (US)

(73) Assignee: United Technologies Corporation, Farmington, CT (US)

( * ) Notice: Subject to any disclaimer, the term of this patent is extended or adjusted under 35 U.S.C. 154(b) by 183 days.

(21) Appl. No.: 14/219,106

(22) Filed: Mar. 19, 2014

(65) Prior Publication Data

US 2014/0294136 A1    Oct. 2, 2014

Related U.S. Application Data

(60) Provisional application No. 61/805,618, filed on Mar. 27, 2013.

(51) Int. Cl.
*G01N 23/04* (2006.01)

(52) U.S. Cl.
CPC .......... *G01N 23/046* (2013.01); *G01N 2223/63* (2013.01)

(58) Field of Classification Search
CPC .......................... G01N 23/046; G01N 2223/63
USPC .................................. 378/20, 53–55, 57–59
See application file for complete search history.

(56) References Cited

U.S. PATENT DOCUMENTS

| | | | |
|---|---|---|---|
| 4,803,639 A | 2/1989 | Steele et al. | |
| 4,969,110 A * | 11/1990 | Little | G01N 23/046 348/26 |
| 4,989,225 A * | 1/1991 | Gupta | G01N 23/043 378/10 |
| 5,119,408 A * | 6/1992 | Little | G01N 23/046 378/10 |
| 5,648,996 A * | 7/1997 | Gupta | G21K 5/10 378/4 |
| 5,848,115 A | 12/1998 | Little et al. | |
| 6,041,132 A * | 3/2000 | Isaacs | G01N 23/046 378/21 |
| 6,459,760 B1 * | 10/2002 | D'Ambrosio | G01N 23/04 356/625 |
| 6,909,768 B2 * | 6/2005 | Takagi | G01N 23/046 378/4 |
| 7,015,473 B2 * | 3/2006 | Harding | G01B 21/085 250/341.1 |
| 7,016,465 B2 * | 3/2006 | Kamegawa | G01N 23/046 378/19 |

(Continued)

FOREIGN PATENT DOCUMENTS

EP    2282050    2/2011

*Primary Examiner* — Allen C. Ho
(74) *Attorney, Agent, or Firm* — Carlson, Gaskey & Olds, P.C.

(57) ABSTRACT

A method of non-destructively inspecting an article includes scanning an article to produce a computerized three-dimensional representation of an internal feature of the article. A measurement characteristic of the internal feature is then generated from a plurality of cross-sections through the computerized three-dimensional representation of the internal feature. The measurement characteristic is then used to determine whether the internal feature meets a design criterion.

14 Claims, 1 Drawing Sheet

(56) References Cited

U.S. PATENT DOCUMENTS

| | | | | |
|---|---|---|---|---|
| 7,254,211 B2* | 8/2007 | Hunt | ................... | G01N 23/046 378/20 |
| 7,286,630 B2* | 10/2007 | Holt | ...................... | A61B 6/032 378/20 |
| 7,356,115 B2* | 4/2008 | Ford | ................... | G01N 23/046 378/4 |
| 7,510,325 B2* | 3/2009 | Endo | ................... | A61B 6/032 250/252.1 |
| 7,602,963 B2 | 10/2009 | Nightingale et al. | | |
| 7,714,304 B2* | 5/2010 | Poglitsch | ............ | G01N 23/046 250/370.09 |
| 7,792,242 B2* | 9/2010 | Kamegawa | ........... | G01N 23/046 378/20 |
| 8,010,315 B2 | 8/2011 | Wu et al. | | |
| 8,102,392 B2* | 1/2012 | Yamagata | ................ | A61B 6/12 345/420 |
| 8,121,247 B2* | 2/2012 | Kunzmann | ........... | G01N 23/046 378/19 |
| 8,160,320 B2* | 4/2012 | Li | ......................... | A61B 6/032 382/128 |
| 8,229,061 B2* | 7/2012 | Hanke | .................. | G01N 23/046 378/20 |
| 8,422,624 B2* | 4/2013 | Christoph | ............. | G01B 15/00 378/4 |
| 8,804,905 B2* | 8/2014 | Christoph | ............. | A61B 6/583 378/19 |
| 8,861,673 B2* | 10/2014 | Michaels | ............. | G01B 15/045 378/4 |
| 9,025,855 B1* | 5/2015 | Christoph | ............ | G01N 23/046 382/152 |
| 9,042,510 B2* | 5/2015 | Voland | ................. | G01N 23/046 378/4 |
| 2009/0109287 A1* | 4/2009 | Sasaki | .................. | G01N 23/046 348/92 |
| 2009/0225954 A1 | 9/2009 | McKim et al. | | |
| 2011/0188626 A1* | 8/2011 | Moriyoshi | ........... | G01N 23/046 378/19 |

* cited by examiner

NON-DESTRUCTIVE INSPECTION OF AN ARTICLE USING CROSS-SECTIONS THROUGH INTERNAL FEATURE

CROSS-REFERENCE TO RELATED APPLICATION

This application claims priority to U.S. Provisional Application No. 61/805,618, which was filed on Mar. 27, 2013.

BACKGROUND

This disclosure relates to non-destructive inspection of an article and, more particularly, to inspection using a computerized three-dimensional representation of an internal feature of the article.

Articles, such as gas turbine engine components, are inspected to ensure that the article meets design geometry or other criteria, for example. The inspection can be relatively complex for articles that include internal features. For example, gas turbine engine airfoils are often designed with positive and negative internal features, such as internal walls and passages, respectively, which must meet certain design criteria.

One technique for inspecting such internal features utilizes a destructive method where the article is physically sectioned and ground-down to reveal the internal geometry of interest in the inspection. However, such a technique, obviously, destroys the article and can require precise sectioning and grinding that are subject to inaccuracies. Moreover, the ground sample does not provide a full representation of the feature because the section is a two-dimensional, single plane through the feature.

SUMMARY

A method of non-destructively inspecting an article according to the present disclosure includes scanning an article to produce a computerized three-dimensional representation of an internal feature of the article, generating a measurement characteristic of the internal feature from a plurality of cross-sections through the computerized three-dimensional representation of the internal feature and using the measurement characteristic to determine whether the internal feature meets a design criterion.

In a further embodiment of any of the foregoing embodiments, the plurality of cross-sections include a first cross-section taken at one end of the internal feature, a second cross-section taken at an opposite end of the internal feature and a third cross-section taken intermediate of the first cross-section and the second cross-section.

In a further embodiment of any of the foregoing embodiments, the plurality of cross-sections are parallel to one another.

In a further embodiment of any of the foregoing embodiments, the measurement characteristic is a central axis of the internal feature.

A further embodiment to any of the foregoing embodiments includes scanning the article using computed tomography scanning.

In a further embodiment of any of the foregoing embodiments, the design criterion is an angular orientation of the internal feature.

A method of non-destructively inspecting an airfoil according to the present disclosure includes scanning an airfoil to produce a computerized three-dimensional representation of an internal passage of the airfoil, generating a measurement axis of the internal passage from a plurality of cross-sections through the computerized three-dimensional representation of the internal passage and using the measurement axis to determine an angular orientation of the internal passage.

In a further embodiment of any of the foregoing embodiments, measurement axis is central axis of the internal passage.

In a further embodiment of any of the foregoing embodiments, the plurality of cross-sections are parallel to one another.

A further embodiment to any of the foregoing embodiments includes, prior to the scanning, orienting the airfoil such that the internal passage is approximately perpendicular to a scanning detector.

In a further embodiment of any of the foregoing embodiments, generating of the measurement axis includes determining a plurality of centerpoints of the internal passage, each of the plurality of centerpoints corresponding to a respective one of the plurality of cross-sections, wherein the measurement axis intersects the plurality of centerpoints.

In a further embodiment of any of the foregoing embodiments, further comprising determining an angle between the measurement axis and a reference axis.

A system for non-destructively inspecting an article according to the present disclosure includes a scanner configured to scan an article and produce a computerized three-dimensional representation of an internal feature of the article. The computerized three-dimensional representation of the internal feature includes a plurality of cross-sections. An analysis processor is configured to generate a measurement characteristic of the internal feature from the plurality of cross-sections.

In a further embodiment of any of the foregoing embodiments, the internal feature is an internal passage and the measurement characteristic is a central axis of the internal passage.

BRIEF DESCRIPTION OF THE DRAWINGS

The various features and advantages of the present disclosure will become apparent to those skilled in the art from the following detailed description. The drawings that accompany the detailed description can be briefly described as follows.

DETAILED DESCRIPTION

Figure 1:
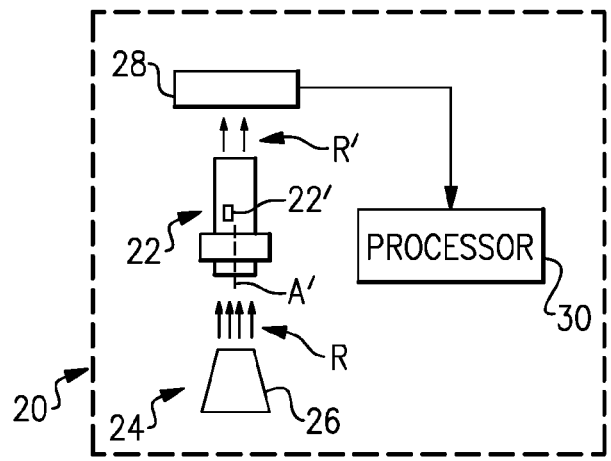
FIG. 1 illustrates an example system for non-destructively inspecting an article.

FIG. 1 schematically illustrates selected portions of an example system 20 for non-destructively inspecting an article, indicated at 22. For instance, the system 20 can be used to inspect an internal feature of the article 22 to determine whether the internal feature meets a design criterion.

The system 20 includes a scanner, generally shown at 24, which is configured to scan the article 22. In this example, the scanner 24 includes a transmitter 26 that is operable to emit radiation R and a detector 28. The detector 28 is operable to receive radiation R' from the article 22 and transmit signals representing the received radiation R' to an analysis processor 30. For example, the analysis processor 30 can include a microprocessor, memory, hardware and/or software to facilitate receiving, processing and analyzing the signals. In a further example, the analysis processor 30 is a computing device.

The scanner 24 is configured to scan the article 22 and produce a computerized three-dimensional representation of the article 22. For instance, the computerized three-dimensional representation at least includes a three-dimensional representation of an internal feature, schematically shown at 22', within the article 22. In one example based upon a gas turbine engine component, the article 22 is an airfoil, such as a cast rotatable blade or a static vane, and the internal feature 22' is a positive or negative internal feature. In a further example, the internal feature 22' includes a wall, an internal passage or both, within the article 22.

The analysis processor 30 is configured to generate a measurement characteristic of the internal feature 22' from a plurality of cross-sections through the computerized three-dimensional representation of the internal feature 22'. For example, the analysis processor 30 includes modeling software, such as UNIGRAPHICS, which enables a user to use the analysis processor 30 to generate the measurement characteristic. In a further example, the scanner 24 is an X-ray scanner, such as a computed tomography (CT) scanner. In such an example, the radiation R and received radiation R' is X-ray radiation and thus the produced computerized three-dimensional representation is an X-ray scan of the article 22.

Figure 2:
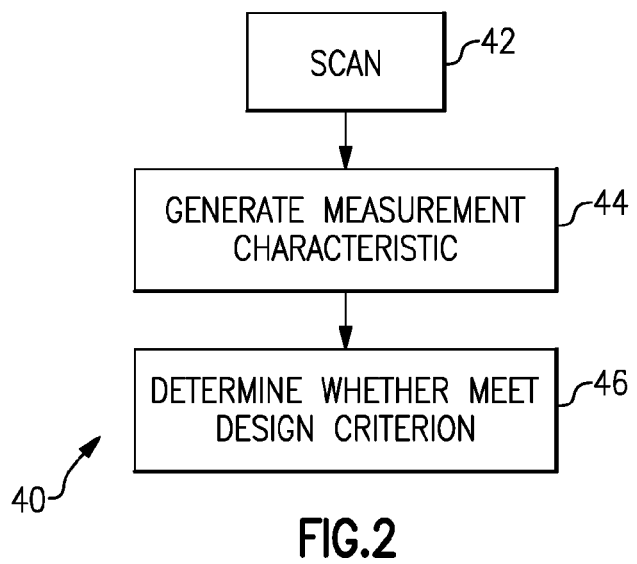
FIG. 2 illustrates a method of non-destructively inspecting an article.

FIG. 2 schematically illustrates an example method 40 of non-destructively inspecting the article 22. Thus, the system 20 can be employed with the method 40, and vice versa. The method 40 includes a scanning step 42, a generating step 44 and a determination step 46. In the scanning step 42, the article 22 is scanned to produce the computerized three-dimensional representation of the internal feature 22' of the article 22. The output of the scanning, i.e., the computerized three-dimensional representation of the internal feature 22', can be represented as a point cloud of the internal feature 22', or alternatively of the entire article 22.

In one example based on a computed tomography scanner, the parameters of the scanning are established to provide high resolution of the internal feature 22' of the article 22. The parameters may be known as CT image reconstruction parameters and are set to provide a maximum pixel size of 0.1 square millimeters (mm$^2$) and a minimum or a low beam-hardening effect.

At the generating step 44, a measurement characteristic of the internal feature 22' is generated from a plurality of cross-sections through the computerized three-dimensional representation of the internal feature 22'. Once the measurement characteristic is generated, the measurement characteristic can be utilized in the determination step 46 to determine whether the internal feature 22' meets a design criterion. For example, the measurement characteristic is compared to a design criterion and a judgment is made of whether the measurement characteristic meets the design criterion. The measurement characteristic can be a geometric characteristic of the internal feature 22', for example.

Figure 3:
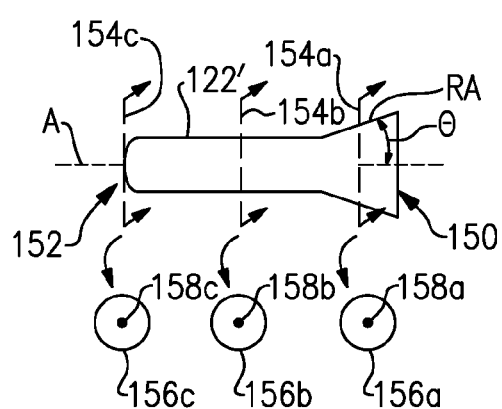
FIG. 3 illustrates an example of a computerized three-dimensional representation of an internal feature of an article.

FIG. 3 schematically shows a computerized three-dimensional representation of an internal feature 122' of an article 22. In this disclosure, like reference numerals designate like elements where appropriate and reference numerals with the addition of one-hundred designate modified elements that are understood to incorporate the same features and benefits of the corresponding elements. In this example, the internal feature 122' is an internal passage of the article 22. The internal passage is generally elongated in this example and spans between a first end 150 and a second, opposed end 152. In this example, a measurement characteristic, measurement axis A, is generated from the computerized three-dimensional representation of the internal feature 122'. The measurement axis A is generated from a plurality of cross-sections, as indicated at 154a, 154b and 154c.

The cross-section 154a is taken at the first end 150 of the internal feature 122'. The cross-section 154c is taken at the second, opposed end 152, and the cross-section 154b is taken intermediate of the ends 150/152. For example, the cross-section 154b is taken within a middle third of the internal feature 122' with respect to a distance between the ends 150/152, such as half-way between the ends 150/152.

Axial views of the cross-sections 154a/154b/154c are shown below the view of the internal feature 122', as indicated at respective cross-sections 156a/156b/156c. In this example, each of the cross-sections 156a/156b/156c is circular and, thus, the passage of the internal feature 122' is cylindrical in shape. It is to be understood however, that the passage could have a different shape and is not limited to cylindrical shapes.

Each of the circular cross-sections 156a/156b/156c has a corresponding centerpoint 158a/158b/158c. The measurement axis A is determined from the centerpoints 158a/158b/158c. In this example, the measurement axis A intersects the centerpoints 158a/158b/158c. It is to be appreciated that, in this example, the three sections 154a/154b/154c were utilized to determine the measurement axis A. Alternatively, only two of the sections could be used or more than three sections could be used.

The measurement axis A represents a centerline of the internal feature 122' and can be used to determine the angular orientation of the internal feature 122'. For example, the measurement axis A can be used to determine an angle θ (Theta) with respect to a reference axis RA. Likewise, the method 40 can be applied to determine angular orientations of other types of passages, walls or other positive or negative features or of other geometric characteristics of interest of the internal feature 122'.

In a further example, to facilitate accurate scanning at step 42 of the method 40, the article 22 is oriented in a particular orientation with respect to the scanner 24. For example, prior to scanning, the article 22 can be oriented in the system 20, using a fixture or the like, with respect to an axis A' (FIG. 1). The axis A' is the axis along which the measurement axis A of the internal feature 122' approximately lies. In one further example, the article 22 is fixed such that the axis A' is within a cone of five degrees or less of the measurement axis A that is later determined using the method 40. In other words, a user of the system 20 and method 40 knows from the design of the article 22 the approximate orientation of the internal feature 22'/122', and thus the approximate orientation that the measurement axis A has, and fixes the article 22 in the system 20 such that the measurement axis A is approximately aligned in a predetermined direction. For example, the axis A' is approximately parallel to the transmitted radiation R direction (or approximately perpendicular to the face of the detector 28). Thus, the radiation R is generally transmitted in a direction parallel the measurement axis A. Such an orientation facilitates obtaining accurate cross-sections through the article 22 with regard to the internal feature 22'/122'.

Although a combination of features is shown in the illustrated examples, not all of them need to be combined to realize the benefits of various embodiments of this disclosure. In other words, a system designed according to an embodiment of this disclosure will not necessarily include all of the features shown in any one of the Figures or all of the portions schematically shown in the Figures. Moreover, selected features of one example embodiment may be combined with selected features of other example embodiments.

The preceding description is exemplary rather than limiting in nature. Variations and modifications to the disclosed examples may become apparent to those skilled in the art that do not necessarily depart from the essence of this disclosure. The scope of legal protection given to this disclosure can only be determined by studying the following claims.

What is claimed is:

1. A method of non-destructively inspecting an article, the method comprising:
   scanning an article to produce a computerized three-dimensional representation of an internal feature of the article;
   generating a measurement characteristic of the internal feature from a plurality of cross-sections through the computerized three-dimensional representation of the internal feature, wherein the measurement characteristic is a central axis of the internal feature; and
   using the measurement characteristic to determine whether the internal feature meets a design criterion.

2. The method as recited in claim 1, wherein the plurality of cross-sections include a first cross-section taken at one end of the internal feature, a second cross-section taken at an opposite end of the internal feature, and a third cross-section taken intermediate of the first cross-section and the second cross-section.

3. The method as recited in claim 1, wherein the plurality of cross-sections are parallel to one another.

4. The method as recited in claim 1, wherein the scanning of the article comprises using computed tomography scanning.

5. The method as recited in claim 1, wherein the design criterion is an angular orientation of the internal feature.

6. The method as recited in claim 1, wherein the generating of the measurement characteristic comprises determining a plurality of centerpoints of the internal feature, each of the plurality of centerpoints corresponding to a respective one of the plurality of cross-sections, and the measurement characteristic is a measurement axis that intersects the plurality of centerpoints.

7. A method of non-destructively inspecting an airfoil, the method comprising:
   scanning an airfoil to produce a computerized three-dimensional representation of an internal passage of the airfoil;
   generating a measurement axis of the internal passage from a plurality of cross-sections through the computerized three-dimensional representation of the internal passage by determining a plurality of centerpoints of the internal passage, each of the plurality of centerpoints corresponding to a respective one of the plurality of cross-sections, wherein the measurement axis interests the plurality of centerpoints; and
   using the measurement axis to determine an angular orientation of the internal passage.

8. The method as recited in claim 7, wherein measurement axis is central axis of the internal passage.

9. The method as recited in claim 7, wherein the plurality of cross-sections are parallel to one another.

10. The method as recited in claim 7, including, prior to the scanning, orienting the airfoil such that the internal passage is approximately perpendicular to a scanning detector.

11. The method as recited in claim 7, further comprising determining an angle between the measurement axis and a reference axis.

12. A system for non-destructively inspecting an article, the system comprising:
    a scanner configured to scan an airfoil article and to produce a computerized three-dimensional representation of an internal passage of the airfoil article, the computerized three-dimensional representation of the internal passage including a plurality of cross-sections there through; and
    an analysis processor configured to generate a measurement axis of the internal passage from the plurality of cross-sections through the computerized three-dimensional representation of the internal passage by determining a plurality of centerpoints of the internal passage, each of the plurality of centerpoints corresponding to a respective one of the plurality of cross-sections, wherein the measurement axis intersects the plurality of centerpoints.

13. The system as recited in claim 12, wherein the analysis processor is configured to determine an angular orientation of the internal passage using the measurement axis.

14. The system as recited in claim 12, wherein the plurality of cross-sections are parallel to one another.

* * * * *